US00PP10367P

United States Patent [19]

Utecht

[11] Patent Number: Plant 10,367

[45] Date of Patent: Apr. 28, 1998

[54] GERANIUM PLANT NAMED 'FISBERNO'

[75] Inventor: Angelika Utecht, Montabaur, Germany

[73] Assignee: Florfis AG, Binningen, Switzerland

[21] Appl. No.: 755,308

[22] Filed: Nov. 22, 1996

[51] Int. Cl.[6] ..... A01H 5/00

[52] U.S. Cl. ..... Plt./87.12

[58] Field of Search ..... Plt./87.12

[56] References Cited

PUBLICATIONS

GTITM UPOVROM citation DE PBR PEL 01001 for 'Fisberno' Dec. 8, 1997.

GTITM UPOVROM Citation CA PBR 96–789 for 'Fisborno' Jul. 29, 1996.

*Primary Examiner*—James R. Feyrer

*Attorney, Agent, or Firm*—Foley & Lardner

[57] ABSTRACT

A new and distinct cultivar of geranium plant named 'Fisberno', particularly characterized by the combined features of light salmon-red flower color, double flower form, bright green foliage with weak zonation, medium to tall, very well branched plant habit, and medium early flower response.

1 Drawing Sheet

The present invention comprises a new and distinct cultivar of geranium, botanically know as *Pelargonium peltatum*, and hereinafter referred to by the cultivar name 'Fisberno'.

'Fisberno' is a product of a planned breeding program which had the objective of creating new geranium cultivars with light red flower color, medium spring flower response, and only moderately vigorous growth.

'Fisberno' was originated from a hybridization made by the inventor Angelika Utecht in a controlled breeding program in Galdar, Gran Canaria, Spain, in 1991. The female parent was a hybrid seedling derived from crossings between the single flowered, rose-red colored cultivar 'Pelenberger', a seedling designated 83/517, and the commercial variety 'Solidor', with 'Solidor' having light pink semi-double flowers, and very compact and bushy plant habit. The male parent 'Fisberno' was 'Fisbing', disclosed in Plant Pat. No. 8,306 and characterized by light red double flowers, medium green foliage and vigorous growth.

'Fisberno' was discovered and selected as one flowering plant within the progeny of the stated cross by Angelika Utecht in 1992 in a controlled environment in Galdar, Gran Canaris, Spain. The first act of asexual reproduction of 'Fisberno' was accomplished when vegetative cuttings were taken from the initial selection in Autumn 1992 in a controlled environement in Galdar, Gran Canaria, Spain, by, or under the supervision of, Angelika Utecht.

Horticultural examination of plants grown from these cuttings, initiated in May 1993 in Hillscheid, Federal Republic of Germany and continuing thereafter, has demonstrated that the combination of characteristics as herein disclosed for 'Fisberno' are firmly fixed and are retained through successive generations of asexual reproduction.

'Fisberno' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Fisberno', which in combination distinguish this geranium as a new and distinct cultivar:

1. Light salmon-red flower color
2. Large double flower
3. Medium green foliage with weak zonation
4. Medium to vigorous growth
5. Very good branching characteristics
6. Medium early flower response Of the many commercial cultivars known to the present inventor, the most similar in comparison to 'Fisberno' are the unpatented cultivar known by the cultivar name 'Guiber' and commercially marketed under the tradename "Bernardo", and the cultivar 'Guitari', disclosed in U.S. Plant Pat. No. 7,360.

Reference is made to attached Chart A which compares certain characteristics of 'Fisberno' to those same characteristics of 'Guiber'. In general comparison to 'Guiber', 'Fisberno' has a slightly lighter flower color, larger and differently shaped flowers, and much more vigorous growth.

In comparison to 'Guitari', 'Fisberno' has a more rose-red, less orange-red hue of flower color, larger inflorescences, smaller leaves with less distinct zonation, and more compact plant habit.

The accompanying photographic drawing shows typical flower and foliage characteristics of 'Fisberno' with colors being as true as possible to illustrations of this type.

In the following description color references are made to The Royal Horticultural Society Colour Chart (R.H.S.). The color values were determined indoors from flowers taken from plants grown in a greenhouse in May 1995 in Hillscheid, Germany.

Classification:

*Botanical.*—A hybrid of the species *Pelargonium peltatum l'hert.*

*Commercial.*—Ivy geranium, cv. 'Fisberno'.

Inflorescence

Umbel:

*Shape.*—Irregular.

*Average diameter.*—105 mm.

*Peduncle length.*132 mm.

*Pedicel length.*—35 mm.

*Pedicel color.*—Mainly green, upper end red.

*Number of flowers per umbel:* 8.5.

Corolla:

*Average diameter.*—58 mm.
*Number of petals.*—about 12–14.
*Number of petaloids.*—3–4.
*Color (general tonality from a distance of three meters)* .—Light salmon red. The flower color tends to fade somewhat with advancing age.
*Color of upper petals.*—52 A.
*Markings on upper petals.*—2 purple veins with lighter spot between, and small purple spot in the middle of the petal.
*Color of lower petals.*—50 A.
*Color of lower surface of petals.*—50 B.
*Color of sepals.*—Light green, largest sepal light red.
*Number of sepals.*—5.

Bud:
*Shape.*—Narrow elliptic.
*Color (adaxial).*—Light green.
*Color (abaxial).*—Salmon.

Reproductive organs:
*Androecium.*—7–8 fertile anthers, white filaments, orange-yellow pollen.
*Gynoecium.*—5–6 lobed stigma, dark red stigma and white filaments.

Spring flowering response period: In Hillscheid, Germany in 1995, plants had on average 0.5 flowers opened 15 weeks after planting of unrooted cuttings (pinched) plants).

Outdoor flower production: The flower count in 1994 in Hillscheid, Germany indicated about 110 umbels per plant for May through August observation period.

Durability: Average shatter resistance, relatively good rain resistance.

Plant:

Foliage:
*Form.*—Ivy shaped.
*Margin.*—Mainly entire.
*Size of leaf.*—85 mm.
*Color of upper surface.*—Light medium green, approximately 137 C-D.
*Color of zonation.*—Brown, weak, about 166 A.
*Tolerance of botrytis.*—Good.

General appearance and form:
*Internode length.*—30–45 mm.
*Branching pattern.*—9.4 branches per plant, based on 16 week old plants.
*Length of plants.*—80 cm, measured in September and based on 35 week old plants.

CHART A

| | 'FISBERNO' | 'GUIBER' |
|---|---|---|
| Flower color: | 50 A–52 A, or lighter | 52 A, or even more intense |
| Flower shape: | 12–14 petals, large flower open in the middle | More than 20 petals, flower small to medium in size and having round, closed shape |
| Diameter of inflorescences | 10.5 cm | 8–9 cm |
| Zonation | Weak | Very weak or absent |
| Growth/Length of plants | 80 cm | 55–60 cm |
| Branching habit (number of branches) | 9.4 | 7.6 |

I claim:

1. A new and distinct cultivar of geranium plant named 'Fisberno', as illustrated and described.

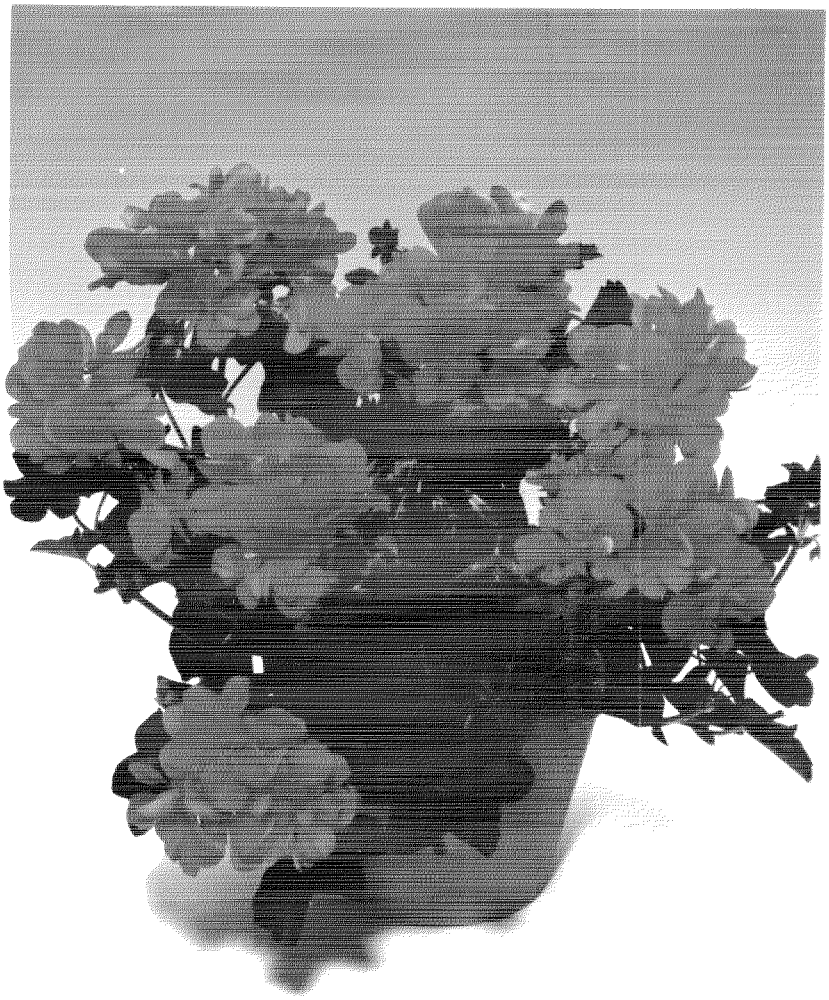

* * * * *